United States Patent [19]

Convers

[11] 4,140,711
[45] Feb. 20, 1979

[54] PREPARATION OF ALKANEDISULFONATES FROM OLEFINS USING CARBOXYLIC ACID

[75] Inventor: Ronald J. Convers, Ponca City, Okla.

[73] Assignee: Continental Oil Company, Ponca City, Okla.

[21] Appl. No.: 891,952

[22] Filed: Mar. 31, 1978

[51] Int. Cl.$^2$ ............................................. C07C 143/04
[52] U.S. Cl. .................................................. 260/513 B
[58] Field of Search .................................... 260/513 B

[56] References Cited

U.S. PATENT DOCUMENTS

| | | | |
|---|---|---|---|
| 2,787,639 | 4/1957 | Sargent | 260/513 B |
| 3,271,444 | 9/1966 | Percival et al. | 260/513 B |
| 3,291,822 | 12/1966 | Baumann et al. | 260/513 B |
| 3,356,717 | 12/1967 | Furrow | 260/513 B |
| 3,729,507 | 4/1973 | Beazley et al. | 260/513 B |
| 3,943,174 | 3/1976 | Ellis et al. | 260/513 B |
| 4,070,396 | 1/1978 | Convers et al. | 260/513 B |

*Primary Examiner*—Joseph E. Evans
*Attorney, Agent, or Firm*—Bayless E. Rutherford, Jr.

[57] ABSTRACT

An improvement in the method of preparing alkanedisulfonates by the reaction of olefins with bisulfite or sulfite is disclosed. The improvement comprises conducting the reaction in the presence of an effective amount of a $C_3$–$C_6$ monocarboxylic acid.

17 Claims, No Drawings

PREPARATION OF ALKANEDISULFONATES FROM OLEFINS USING CARBOXYLIC ACID

GENERAL BACKGROUND

Alkanedisulfonates are known to be useful as water-soluble detergents and as phosphate-free detergent builders. A typical method of preparing alkanedisulfonates comprises reacting alpha or internal olefins (usually $C_{15}$–$C_{22}$) with 2 equivalents of water soluble bisulfite in aqueous alcoholic solutions having a pH of 3.5 to 5.

I have discovered a method of preparing alkanedisulfonates which does not use an aqueous alcohol solution. Briefly, my method comprises reacting the olefins and bisulfite in the presence of a $C_3$–$C_6$ monocarboxylic acid. My process is not only novel; in many instances my process provides improved results such as rate acceleration and yield improvement.

It is of interest that I have found that acetic acid does not work nearly as well in my process as do the $C_3$–$C_6$ monocarboxylic acids.

BRIEF SUMMARY OF THE INVENTION

Broadly stated, my invention is directed to a method of preparing alkanedisulfonates wherein the method comprises:
(A) forming an admixture comprising
  (1) $C_2$–$C_{40}$ olefin
  (2) $C_3$–$C_6$ monocarboxylic acid
  (3) alkali metal bisulfite or sulfite, and
(B) adding to the reaction admixture of step (A) an effective amount of free radical initiating means.

In a preferred embodiment the reaction admixture contains a controlled amount of water, expressed as water-carboxylic acid ratio.

Also, in a preferred embodiment the admixture of step (A) contains a controlled ratio of bisulfite to sulfite.

DETAILED DESCRIPTION

Suitable olefins for use in my process contain from 2 to about 40 carbon atoms, preferably from about 10 to about 36 carbon atoms. Preferably, the olefins are linear. Also, the double bond can be either alpha or internal.

Suitable carboxylic acids are $C_3$–$C_6$ monocarboxylic, which can be straight or branched-chain.

The amount of acid, expressed as acid to olefin, suitably is in the range of about 100 grams to about 2500 grams per mole of olefin. On the same basis preferably the amount of acid is in the range of about 1200 to about 1600 grams per mole.

While the reaction is operable in the absence of water, preferably water is used in the reaction. The preferred amount of water, on a volume basis, expressed as water to acid is in the range of 0.05:1 to 0.2:1. Suitably, the amount of water may range up to 1 volume per volume of acid.

Both alkali metal bisulfite and alkali metal sulfite can be used in the process. The preferred alkali metal is sodium because of availability and cost. The amount of bisulfite and/or sulfite which suitably can be used in the process, expressed as moles per mole of olefin, is in the range of about 5:1 to about 1:1. Preferably, on the same basis, the amount of bisulfite and/or sulfite is in the range of about 2:1 to about 4:1.

For some reason, the process works better when a controlled ratio of bisulfite to sulfite is employed. Preferably, the moles of bisulfite to moles of sulfite is in the range of about 0.8:1 to about 2:1.

Free radical initiating means are used in my process. Knowing that free radical initiating means are used any person skilled in the art can readily select one and the amount.

Examples of free radical initiator includes oxygen, air (which contains oxygen), organic peroxides such as benzoyl peroxide and lauroyl peroxide; peroxy dicarbonates, such as diisopropyl peroxydicarbonate, di-2-ethylhexylperoxydicarbonate, di-sec-butyl-peroxydicarbonate, di(n-propyl)peroxydicarbonate, dicetyl peroxydicarbonate; peroxy esters, such as t-butyl peroxyneodecanoate, t-butyl peroxypivalate, 2,5-dimethyl-2,5-bis(2-ethyl-hexanoylperoxy)hexane and t-butyl peroctoate; azo compounds, such as azobisisobutyronitrile.

When oxygen is used as the free radical means a suitable amount is in the range of about 0.5:1 to about 0.05:1, expressed as moles of oxygen to moles of olefin. On the same basis a preferable amount is in the range of about 0.15:1 to about 0.35:1.

Other free radical initiating means such as gamma radiation can also be used.

A water soluble dispersant (e.g. sodium alkylbenzenesulfonate) can be used in my process. Such a material is not necessary, however.

In many cases a paraffin is added to the reaction as an internal GLC (gas liquid chromatography) standard. It is understood that such use is not necessary to the process. When a paraffin is used for this purpose the only requirement is that it be a different molecular weight than that of the olefin used.

Temperature is not a critical feature of the process. For reasons of convenience ambient temperatures (e.g. 25°–35° C.) are usually employed. Use of a higher temperature requires use of a reaction vessel capable of withstanding higher pressures.

Usually the process is run at ambient pressure. Superatmospheric pressure can be used, which provides improved results when reaction temperatures higher than ambient are used.

Time is not critical in the process. The process is usually conducted until a desired olefin conversion is obtained. The time is dependent on initiation rate and molecular weight of the olefin.

The disulfonate products can be isolated by methods known in the art. When low volume ratios of water to acid are used, suitable desalting can be done by decantation or filtration of a crude liquid product. The olefins can be recovered either by low temperature vacuum distillation of the crude product or by common extractive deoiling techniques. The acid can be recovered by distillation.

In order to illustrate the nature of the present invention still more clearly the following examples will be given. It is to be understood, however, that the invention is not to be limited to the specific conditions or details set forth in these examples except insofar as such limitations are specified in the appended claims.

Examples 1–6 used a mixed $C_{12}$ linear internal olefin which was prepared by isomerizing alpha-olefins using $Fe(CO)_5$.

EXAMPLE 1

This example is comparative and shows the results obtained using acetic acid.

To a 500 ml Morton flask were added the following materials: 8.4 g of olefins, 0.84 g of n-tetradecane, 13.3 g of $NaHSO_3$, 8.0 g of $Na_2SO_3$, 20.0 g of 51.6 percent sodium alkylbenzenesulfonates (MW = 340) in water, and 80 ml of glacial acetic acid. The admixture was stirred at 2,000 RPM under nitrogen for 15 minutes. Nitrogen flow was then stopped. Reaction was initiated at ambient temperature and pressure by a 1 ml/min air flow into the admixture using a sintered glass sparger. The reaction was stopped after 6 hours. Olefin conversion was 10 percent.

EXAMPLE 2

Example 1 was repeated except that 80 ml of propionic acid was used instead of acetic acid. Olefin conversion after 6 hours was 92 percent.

EXAMPLE 3

The following materials were added to a 500 ml Morton flask: 8.4 g of olefins, 0.84 g of n-tetradecane, 13.3 g of $NaHSO_3$, 8.0 g of $Na_2SO_3$, 10 ml of water, 20.0 g of 51.6 percent sodium alkylbenzenesulfonates (MW = 340) in water, and 70 ml of propionic acid. The admixture was stirred at 2,000 RPM under nitrogen for 15 minutes. Nitrogen flow was then stopped. Reaction was initiated at ambient temperature and pressure by a 1 ml/min air flow into the admixture using a sintered glass sparger. Reaction was terminated after 6 hours. Olefin conversion was 93 percent.

EXAMPLE 4

Example 2 was repeated except that 40 ml of water and 40 ml of propionic acid were used instead of 80 ml of propionic acid. Olefin conversion after 6 hours was 30 percent.

EXAMPLE 5

Example 3 was repeated except that 70 ml of butyric acid was used instead of propionic acid. Olefin conversion after 4.3 hours was 85 percent.

EXAMPLE 6

Example 3 was repeated except that 70 ml of isobutyric acid was used instead of propionic acid. Olefin conversion after 4.3 hours was 86 percent.

EXAMPLE 7

This example used a mixed $C_{15}$–$C_{18}$ linear internal olefin prepared by catalytic dehydrogenation of a mixture of $C_{15}$–$C_{18}$-normal paraffins. No surfactant was used in this example.

To a 500 ml Morton flask were added the following materials: 11.2 g of olefins, 1.12 g of n-dodecane, 13.3 g of $NaHSO_3$, 8.0 g of $Na_2SO_3$, 14 ml of water, and 74 ml of propionic acid. The admixture was stirred at 2,000 RPM under nitrogen for 15 minutes. Nitrogen flow was then stopped. Reaction was initiated at ambient temperature and pressure by a 1 ml/min air flow into the liquid using a sintered glass sparger. Reaction was terminated after 6 hours. Olefin conversions were the following:

$C_{15}$: 82%
$C_{16}$: 81%
$C_{17}$: 79%
$C_{18}$: 79%

The deoiled, desalted, and dried product showed 75.24% active, 0.98% oil, 2.47% $Na_2SO_4$, 10% sulfur (x-ray fluorescence), and 90–95% disulfonate (tlc).

EXAMPLE 8

This example used mixed $C_{18}$ linear internal olefins produced by catalytic dehydrogenation of n-octadecane.

The following materials were added to a 500 ml Morton flask: 126 g of olefins, 72.5 g of $NaHSO_3$, 25.1 g of $Na_2SO_3$, 200 ml of propionic acid and 40.5 ml of water. The admixture was stirred at 2,000 RPM at ambient temperature and pressure. Reaction was initiated using an approximately 31 ml/min air flow into the liquid. The reaction mixture set up to a paste in 2.6 hours. Olefin conversion was 98 percent.

EXAMPLE 9

This example is comparative and shows the results obtained using aqueous alcohol as the solvent.

The following materials were added to a 500 ml Morton flask: 12.6 g of 1-octadecene, 1.26 g of n-dodecane, 13.3 g of $NaHSO_3$, 8.0 g of $Na_2SO_3$, 40 ml of 1-propanol, 40 ml of water, 4 ml of liquid $SO_2$ and 1 g of 50 percent aqueous NaOH (to provide a pH of 4). The admixture was stirred at 2,000 RPM at ambient temperature and pressure. Reaction was initiated using a 3.7 ml/min air flow into the admixture. The pH of the admixture was maintained at 4 (glass electrode) by periodic addition of several drops of 50 percent aqueous NaOH. After 1 and 2 hours olefin conversions were 10 percent and 12 percent, respectively.

EXAMPLE 10

This example illustrates the improved results obtained using a carboxylic acid.

The following materials were added to a 500 ml Morton flask: 12.6 g of 1-octadecene, 1.26 g of n-dodecane, 13.3 g of $NaHSO_3$, 8.0 g of $Na_2SO_3$, 74 ml of propionic acid, 14 ml of water and 3.5 ml of 50 percent aqueous NaOH (to reach pH 4). The admixture was stirred at 2,000 RPM at ambient temperature and pressure. The reaction was initiated by a 3.7 ml/min air flow into the admixture. Olefin conversion after 1, 2 and 3 hours were 21 percent, 33 percent, and 51 percent, respectively.

EXAMPLE 11

This example used a mixture of $C_{24\text{-}30}$ alpha-olefins having the following composition as shown by GLC analysis.

| Alpha-Olefin | Area Percent |
| --- | --- |
| $C_{24}$ | 32.58 |
| $C_{26}$ | 31.05 |
| $C_{28}$ | 17.08 |
| $C_{30}$ | 6.19 |

The following materials were added to a 500 ml Morton flask: 36.0 g of olefins, 3.6 g of n-tetradecane, 26.0 g of $NaHSO_3$, 26 ml of water, and 150 ml of propionic acid. The admixture was stirred at 2,000 RPM at ambient temperature and pressure. Reaction was initiated by 5 ml/min air flow into the admixture. The reaction was terminated after 13 hours. Olefin conversions were as follows:

| Alpha-Olefin | Percent Olefin Conversion |
| --- | --- |
| $C_{24}$ | 35 |
| $C_{26}$ | 30 |
| $C_{28}$ | 28 |

| Alpha-Olefin | Percent Olefin Conversion |
| --- | --- |
| $C_{30}$ | 23 |

Thus, having described the invention in detail, it will be understood by those skilled in the art that certain variations and modifications may be made without departing from the spirit and scope of the invention as defined herein and in the appended claims.

I claim:

1. A method of preparing alkanedisulfonates, said method comprising:
   (A) forming a reaction admixture comprising
      (1) $C_2$–$C_{40}$ olefin, which is alpha or internal,
      (2) a $C_3$–$C_6$ monocarboxylic acid, wherein the amount of acid is in the range of about 100 to about 2500 grams per mole of olefin,
      (3) an alkali metal bisulfite and/or alkali metal sulfite, wherein the amount expressed as mole per mole of olefin is in the range of about 5:1 to 1:1, and
   (B) adding to the reaction mixture of step (A) an effective amount of free radical initiating means.

2. The method of claim 1 wherein the reaction admixture of step (A) contains up to 1 volume part of water per part of acid.

3. The method of claims 1 or 2 wherein the admixture contains a ratio of bisulfite to sulfite, on a molar basis, in the range of 0.8:1 to 2:1.

4. The method of claim 1 wherein the alkali metal of said bisulfite and sulfite is sodium.

5. The method of claim 4 wherein the olefin contains about 10 to about 36 carbon atoms and is linear.

6. The method of claim 5 wherein the amount of water, on a volume basis, expressed as water to acid, is in the range of about 0.05:1 to 0.2:1.

7. The method of claim 6 wherein the free radical initiating means is oxygen and the amount of oxygen, expressed as moles of oxygen to moles of olefin, is in the range of about 0.05:1 to about 0.5:1.

8. The method of claim 7 wherein the olefin contains about 12 to about 30 carbon atoms.

9. The method of claim 8 wherein the monocarboxylic acid is propionic acid.

10. The method of claim 9 wherein the monocarboxylic acid contains 4 carbon atoms.

11. The method of claim 3 wherein the alkali metal of said bisulfite and sulfite is sodium.

12. The method of claim 11 wherein the olefin contains about 10 to about 36 carbon atoms and is linear.

13. The method of claim 12 wherein the amount of water on a volume basis, expressed as water to acid, is in the range of about 0.05:1 to 0.2:1.

14. The method of claim 13 wherein the free radical initiating means is oxygen and the amount of oxygen, expressed as moles of oxygen to moles of olefin, is in the range of about 0.05:1 to about 0.5:1.

15. The method of claim 14 wherein the olefin contains about 12 to about 30 carbon atoms.

16. The method of claim 15 wherein the monocarboxylic acid is propionic acid.

17. The method of claim 16 wherein the monocarboxylic acid contains 4 carbon atoms.